(12) United States Patent
Kurahashi et al.

(10) Patent No.: US 8,324,131 B2
(45) Date of Patent: Dec. 4, 2012

(54) COMPOSITION AND METHOD FOR CONTROLLING PLANT DISEASES

(75) Inventors: Makoto Kurahashi, Nishinomiya (JP); Yuichi Matsuzaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 6 days.

(21) Appl. No.: 13/131,082

(22) PCT Filed: Nov. 20, 2009

(86) PCT No.: PCT/JP2009/070076
§ 371 (c)(1), (2), (4) Date: Jul. 22, 2011

(87) PCT Pub. No.: WO2010/061942
PCT Pub. Date: Jun. 3, 2010

(65) Prior Publication Data
US 2012/0004099 A1 Jan. 5, 2012

(30) Foreign Application Priority Data
Nov. 25, 2008 (JP) ................. 2008-299275

(51) Int. Cl.
*A01N 43/78* (2006.01)
*A01N 43/653* (2006.01)
*A01P 3/00* (2006.01)

(52) U.S. Cl. ............ 504/100; 514/370; 514/383
(58) Field of Classification Search ............... 504/100; 514/370, 383
See application file for complete search history.

(56) References Cited

U.S. PATENT DOCUMENTS

| 5,514,643 | A | 5/1996 | Rew et al. |
| 6,740,671 | B2 * | 5/2004 | Kang et al. ............ 514/370 |
| 2006/0281766 | A1 | 12/2006 | Blasco et al. |
| 2008/0200334 | A1 | 8/2008 | Blasco et al. |

FOREIGN PATENT DOCUMENTS

EP 0 488 395 6/1992

OTHER PUBLICATIONS

International Search Report issued Dec. 28, 2009 in International (PCT) Application No. PCT/JP2009/070076.

* cited by examiner

*Primary Examiner* — John Pak
(74) *Attorney, Agent, or Firm* — Wenderoth, Lind & Ponack, L.L.P.

(57) ABSTRACT

Disclosed is a composition for controlling plant diseases, which contains ethaboxam and metconazole as active ingredients. Also disclosed is a method for controlling plant diseases, which is characterized in that effective amounts of ethaboxam and metconazole are applied to a plant or the soil where the plant grows.

6 Claims, No Drawings

COMPOSITION AND METHOD FOR CONTROLLING PLANT DISEASES

TECHNICAL FIELD

The present invention relates to a composition for controlling plant diseases and a method for controlling plant diseases.

BACKGROUND ART

Ethaboxam (see, for example, KR-B-0124552) and metconazole ("The Pesticide Manual—14th edition" published by BCPC, ISBN: 1901396142) are conventionally known as active ingredients of agents for controlling plant diseases. Nevertheless, there is a continuing need for more highly active agents for controlling plant diseases.

DISCLOSURE OF INVENTION

An object of the present invention is to provide a composition for controlling plant diseases and a method for controlling plant diseases and so on, having excellent control effect for plant diseases.

The present invention provides a composition for controlling plant diseases and a method for controlling plant diseases, having an improved control effect for plant diseases by combining ethaboxam with metconazole.

Specifically, the present invention takes the following constitutions.

[1] A composition for controlling plant diseases comprising, as active ingredients, ethaboxam and metconazole;

[2] The composition according to [1], which has a weight ratio of ethaboxam to metconazole falling within the range of from 1:0.01 to 1:50;

[3] A seed treatment agent comprising, as active ingredients, ethaboxam and metconazole;

[4] A plant seed treated with effective amounts of ethaboxam and metconazole;

[5] A method for controlling plant diseases which comprises applying, to a plant or a locus where a plant is allowed to grow, effective amounts of ethaboxam and metconazole;

[6] A method for controlling plant diseases according to [5], wherein the plant diseases are plant diseases caused by *Oomycetes*; and

[7] Combined use for controlling plant diseases of ethaboxam and metconazole; and so on.

The composition according to the present invention exhibits an excellent control effect for plant diseases.

MODES FOR CARRYING OUT THE INVENTION

Ethaboxam for use in the composition for controlling plant diseases according to the present invention is a compound described in KR-B-0124552 and can be synthesized, for example, by a method described in KR-B-0124552.

Metconazole for use in the composition for controlling plant diseases according to the present invention is a known compound and described, for example, in "The Pesticide Manual—14th edition" published by BCPC, ISBN: 1901396142, pp. 689. The compound can be obtained from commercial agents or prepared using well-known methods.

In the composition for controlling plant diseases according to the present invention, the weight ratio of ethaboxam to metconazole is typically in the range of 1:0.01 to 1:50, preferably 1:0.05 to 1:20, more preferably 1:0.25 to 1:10.

The composition for controlling plant diseases according to the present invention may be a simple mixture of ethaboxam and metconazole. Alternatively, the composition for controlling plant diseases is typically produced by mixing ethaboxam and metconazole with an inert carrier, and adding to the mixture a surfactant and other adjuvants as needed so that the mixture can be formulated into an oil agent, an emulsion, a flowable agent, a wettable powder, a granulated wettable powder, a powder agent, a granule agent and so on. The composition for controlling plant diseases mentioned above can be used as a seed treatment agent of the present invention as it is or added with other inert ingredients.

In the composition for controlling plant diseases according to the present invention, the total amount of ethaboxam and metconazole is typically in the range of 0.1 to 99% by weight, preferably 0.2 to 906 by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The composition for controlling plant diseases according to the present invention is effective for the following plant diseases.

Diseases of rice: blast (*Magnaporthe grisea*), Helminthosporium leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), Fusarium head blight (*Fusarium graminearum, F. avenacerum, F. culmorum, Microdochium nivale*), rust (*Puccinia striiformis, P. graminis, P. recondita*), pink snow mold (*Micronectriella nivale*), Typhula snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodoru*), and yellow spot (*Pyrenophora tritici*-repentis).

Diseases of barley: powdery mildew (*Erysiphe graminis*), Fusarium head blight (*Fusarium graminearum, F. avenacerum, F. culmorum, Microdochium nivale*), rust (*Puccinia*

*striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and *Rhizoctonia* damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae*-maydis), and *Rhizoctonia* damping-off (*Rhizoctonia solani*).

Diseases of citrus: melanose (*Diaporthe citri*), scab (*Elsinoe fawcetti*), penicillium rot (*Penicillium digitatum, P. italicum*), and brown rot (*Phytophthora parasitica, Phytophthora citrophthora*).

Diseases of apple: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), crown rot (*Phytophtora cactorum*), brown leaf spot (*Diplocarpon mali*), ring rot (*Botryosphaeria berengeriana*), and violet root rot (*Helicobasidium mompa*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

Diseases of peach: brown rot (*Monilinia fructicola*), scab (*Cladosporium carpophilum*), and *phomopsis* rot (*Phomopsis* sp.).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), *Fusarium* wilt (*Fusarium oxysporum*), downy mildew (*Pseudoperonospora cubensis*), *Phytophthora* rot (*Phytophthora* sp.), and damping-off (*Pythium* sp.);

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: *Alternaria* leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scad (*Elsinoe glycines*), pod and stem blight (*Diaporthe phaseolorum* var. sojae), *septoria* brown spot (*Septoria glycines*), frogeye leaf spot (*Cercospora sojina*), rust (*Phakopsora pachyrhizi*), brown stem rot (*Phytophthora sojae*), and *Rhizoctonia* damping-off (*Rhizoctonia solani*).

Diseases of kidney bean: anthracnose (*Colletotrichum lindemthianum*).

Diseases of peanut: leaf spot (*Cercospora personata*), brown leaf spot (*Cercospora arachidicola*) and southern blight (*Sclerotium rolfsii*).

Diseases of garden pea: powdery mildew (*Erysiphe pisi*), and root rot (*Fusarium solani* f. sp. pisi).

Diseases of potato: early blight (*Alternaria solani*), late blight (*Phytophthora infestans*), pink rot (*Phytophthora erythroseptica*), powdery scab (*Spongospora subterranean* f. sp. subterranea), and black scurf (*Rhizoctonia solani*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis* sp.), and anthracnose (*Colletotrichum theaesinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: *sclerotinia* rot (*Sclerotinia sclerotiorum*), and *Rhizoctonia* damping-off (*Rhizoctonia solani*).

Diseases of cotton: *Rhizoctonia* damping-off (*Rhizoctonia solani*).

Diseases of sugar beat: *Cercospora* leaf spot (*Cercospora beticola*), leaf blight (*Rhizoctonia solani*), root rot (*Rhizoctonia solani*), and *Aphanomyces* root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of *chrysanthemum* and asteraceous plants: downy mildew (*Bremia lactucae*), leaf blight (*Septoria chrysanthemi*-indici), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), *Sclerotinia* rot (*Sclerotinia sclerotiorum*), and southern blight (*Sclerotium rolfsii*).

Disease of Japanese radish: *Alternaria* leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Seed diseases or diseases in the early stages of the growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. and *Diplodia* spp.

Viral diseases of various plants mediated by *Polymixa* spp. or the *Olpidium* spp. and so on.

Among the above, examples of diseases for which high control effects of the present invention are expected include damping-off and root rot of wheat, barley, corn, rice, sorghum, soybean, cotton, rapeseed, sugar beat and turfgrass to caused by *Pythium* spp. (*Pythium aphanidermatum, Pythium debarianum, Pythium graminicola, Pythium irregulare, Pythium ultimum*); seed diseases or diseases in the early stages of the growth of wheat, barley, corn, cotton, soybean, rapeseed and turfgrass caused by *Fusarium* spp. (*Fusarium* spp.); bakanae disease (*Gibberella fujikuroi*) of rice; powdery mildew (*Erysiphe graminis*), *Fusarium* head blight (*Fusarium graminearum, F. avenacerum, F. culmorum, Microdochium nivale*), rust (*Puccinia striiformis, P. graminis, P. recondita*), loose smut (*Ustilago tritici*), bunt (*Tilletia caries*), leaf blotch (*Mycosphaerella graminicola*) of wheat; powdery mildew (*Erysiphe graminis*), *Fusarium* head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*) of barley;

smut (*Ustilago maydis*), southern rust (*Puccinia polysora*), gray leaf spot (*Cercospora zeae*-maydis) of corn; *sclerotinia* rot (*Sclerotinia sclerotiorum*) of rapeseed; *Aphanomyces* root rot (*Aphanomyces cochlioides*) of sugar beat; brown patch and large patch (*Rhizoctonia solani*), dollar spot (*Sclerotinia homeocarpa*) of turfgrass; rust (*Phakopsora pachyrhizi*), brown stem rot (*Phytophthora sojae*) of soybean; black shank (*Phytophthora nicotianae*) of tobacco; downy mildew (*Plasmopara halstedii*) of sunflower; late blight (*Phytophthora infestans*) of potato; powdery mildew (*Uncinula necator*) of grape; scab (*Venturia inaequalis*) and powdery mildew (*Podosphaera leucotricha*) of apple.

Among the above, particularly high control effects of the present invention are expected for foliage diseases, soilborne diseases and seed-borne diseases of various plants caused by *Oomycetes*.

In the case of spray treatment, examples of plant diseases for which high control effects of the present invention are expected include brown stem rot (*Phytophthora sojae*) of soybean, black shank (*Phytophthora nicotianae*) of tobacco, downy mildew (*Plasmopara halstedii*) of sunflower, and late blight (*Phytophthora infestans*) of potato.

In the case of treatment of seed, bulb or the like, examples of plant diseases for which high control effects of the present invention are expected include damping-off and root rot of wheat, barley, corn, rice, sorghum, soybean, cotton, rapeseed, sugar beat and turfgrass caused by *Pythium* spp. (*Pythium aphanidermatum, Pythium debarianum, Pythium graminicola, Pythium irregulare, Pythium ultimum*), brown stem rot of soybean, black shank of tobacco, downy mildew of sunflower, and *Aphanomyces* root rot (*Aphanomyces cochlioides*) of sugar beat.

Plant diseases can be controlled by applying effective amounts of ethaboxam and metconazole to the plant pathogens or a place where the plant pathogens inhabit or a place (plant, soil) where the plant pathogens may inhabit.

Plant diseases can be controlled by applying effective amounts of ethaboxam and metconazole to a plant or a place where a plant is allowed to grow. As a plant which is the object of application, stalk and leaves of the plant, seed of the plant, bulbs of the plant can be included. Here, the bulb means a bulb, corm, rhizoma, stem tuber, root tuber and rhizophore.

When the application is conducted to plant diseases, a plant or the soil where the plant is allowed to grow, ethaboxam and metconazole may be separately applied for the same period, but they are typically applied as a composition for controlling plant diseases of the present invention from the viewpoint of simplicity of the application.

The controlling method of the present invention includes treatment of stalk and leaves of a plant, treatment of the place where the plant is allowed to grow such as the soil, treatment of the seeds such as seed sterilization/seed coating and treatment of the bulb such as potato sets.

As the treatment of stalk and leaves of a plant in the control method of the present invention, specifically, for example, application onto the surface of the plant such as spraying to the stalk and leaves and spraying to the trunk can be included.

As the treatment of the soil in the control method of the present invention, for example, spraying onto the soil, admixing with the soil, perfusion of an agent liquid into the soil (irrigation of an agent liquid, injection into the soil, dripping of an agent liquid) can be included and the examples of the place to be treated include a planting hole, a furrow, peripheral of the planting hole, peripheral of the planting furrow, the entire surface of the growing area, the parts between the soil and the plant, area between roots, area beneath the trunk, main furrow, growing soil, box for raising seedlings, tray for raising seedlings, seedbed. The treatment can be performed before dissemination, at the time of dissemination, immediately after the dissemination, during the raising period of seedlings, before settled planting, at the time of settled planting and growing time after settled planting. In the soil treatment mentioned above, the active ingredients may be applied to the plant at the same time, or solid manure such as paste manure containing the active ingredients may be applied to the soil. The active ingredients may be mixed in irrigating liquid, and, for example, may be injected to irrigating facilities (irrigating tube, irrigating pipe, sprinkler, etc.), mixed into the flooding liquid between furrows, or mixed into a water culture medium. Alternatively, the irrigating liquid and the active ingredients may be mixed beforehand and, for example, used for treatment by an appropriate irrigating method including the irrigating method mentioned above and the other methods such as sprinkling and flooding.

Treatment of a seed in the control method of the present invention is, for example, a method for treating a seed, a bulb or the like to be protected from plant diseases with a composition for controlling plant diseases of the present invention and specific examples thereof include a spraying treatment in which a suspension of the composition for controlling plant diseases of the present invention is atomized and sprayed on the seed surface or the bulb surface; smearing treatment in which a wettable powder, an emulsion, a flowable agent or the like of the composition for controlling plant diseases of the present invention as it is or added with a small amount of water is applied on the seed surface or the bulb surface; immersing treatment in which the seed is immersed in a solution of the composition for controlling plant diseases of the present invention for a certain period of time; film coating treatment and pellet coating treatment.

When a plant or the soil for growing a plant is treated with ethaboxam and metconazole, the amount for the treatment may be changed depending on the kind of the plant to be treated, the kind and the occurring frequency of the diseases to be controlled, formulation form, treatment period, climatic condition and so on, but the total amount of ethaboxam and metconazole (hereinbelow referred to as the amount of the active ingredients) per 10,000 $m^2$ is typically 1 to 5000 g and preferably 2 to 400 g.

The emulsion, wettable powder, flowable agent or the like is typically diluted with water, and then sprinkled for treatment. In this case, the concentration of the active ingredients is typically in the range of 0.0001 to 3% by weight and preferably 0.0005 to 1% by weight. The powder agent, granule agent or the like is typically used for treatment without dilution.

In the treatment of seeds, the amount of the applied active ingredients is typically in the range of 0.001 to 20 g, preferably 0.01 to 5 g per 1 kg of seeds.

In the composition for controlling plant diseases according to the present invention, other azole fungicides may be used in combination with ethaboxam, instead of metconazole. Examples of said azole fungicides include bromuconazole, cyproconazole, difenoconazole, diniconazole, epoxiconazole, fluquinconazole, flusilazole, fuberidazole, ipconazole, prochloraz, prothioconazole, tebuconazole, triticonazole, triadimenol, triadimefon, and imazalil. It is however preferable to use ethaboxam in combination with metconazole as in the composition for controlling plant diseases according to the present invention.

The control method of the present invention can be used in agricultural lands such as fields, paddy fields, lawns and orchards or in non-agricultural lands.

The present invention can be used to control diseases in agricultural lands for cultivating the following "plant" and the like without adversely affecting the plant and so on.

Examples of the crops are as follows:

crops: corn, rice, wheat, barley, rye, oat, sorghum, cotton, soybean, peanut, buckwheat, beet, rapeseed, sunflower, sugar cane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, colocasia, etc., flowers, foliage plants, turf grasses, fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc., trees other than fruit trees; tea, mulberry, flowering plant, roadside trees (ash, birch, dogwood, Eucalyptus, Ginkgo biloba, lilac, maple, Quercus, poplar, Judas tree, *Liquidambar formosana*, plane tree, zelkova, *Japanese arborvitae*, fir wood, hemlock, juniper, Pinus, *Picea*, and *Taxus cuspidate*), etc.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, PPO inhibitors such as flumioxazin, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soy bean on which resistance to sulfonylurea ALS inhibitory herbicides such as thifensulfuron-methyl has been conferred by a classical breeding method, which is already commercially available under a product name of STS soy bean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soy bean, cotton, rape, sugar beet resistant to glyphosate, which is already commercially available under a product name of RoundupReady (registered trademark), AgrisureGT, etc. Similarly, there are corn, soy bean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to *Coleoptera, Hemiptera, Diptera, Lepidoptera* and *Nematodes*, to the plants. Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soy bean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

EXAMPLES

While the present invention will be more specifically described by way of formulation examples, seed treatment examples, and test examples in the following, the present invention is not limited to the following examples. In the following examples, the part represents part by weight unless otherwise noted in particular.

Formulation Example 1

Fully mixed are 2.5 parts of metconazole, 1.25 parts of ethaboxam, 14 parts of polyoxyethylene styrylphenyl ether, 6 parts of calcium dodecyl benzene sulfonate and 76.25 parts of xylene, so as to obtain an emulsion.

Formulation Example 2

Five (5) parts of metconazole, 5 parts of ethaboxam, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain a flowable formulation.

Formulation Example 3

Five (5) parts of metconazole, 10 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Formulation Example 4

Five (5) parts of metconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Formulation Example 5

Forty (40) parts of metconazole, 5 parts of ethaboxam, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and a flowable formulation is obtained.

Formulation Example 6

Fifty (50) parts of metconazole, 0.5 part of ethaboxam, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix is ground with a jet mill so as to obtain powders.

Formulation Example 7

One (1) part of metconazole, 4 parts of ethaboxam, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain granules.

Formulation Example 8

One (1) part of metconazole, 40 parts of ethaboxam, 3 parts of calcium lignin sulfonate, 2 parts of sodium lauryl sulfate and 54 parts of synthetic hydrated silicon oxide are fully ground and mixed so as to obtain wettable powders.

Formulation Example 9

One (1) part of metconazole, 2 parts of ethaboxam, 87 parts of kaolin clay and 10 parts of talc are fully ground and mixed so as to obtain powders.

Formulation Example 10

Two (2) parts of metconazole, 0.25 part of ethaboxam, 14 parts of polyoxyethylene styrylphenyl ether, 6 parts of calcium dodecyl benzene sulfonate and 77.75 parts of xylene are fully mixed, so as to obtain an emulsion.

Formulation Example 11

Ten (10) parts of metconazole, 2.5 parts of ethaboxam, 1.5 parts of sorbitan trioleate, 30 parts of an aqueous solution containing 2 parts of polyvinyl alcohol are subjected to fine grinding according to a wet grinding method. Thereafter, 47.5 parts of an aqueous solution containing 0.05 part of Xanthan gum and 0.1 part of aluminum magnesium silicate is added to the ground solution, and 10 parts of propylene glycol is further added thereto. The obtained mixture is blended by stirring, so as to obtain a flowable formulation.

Formulation Example 12

One (1) part of metconazole, 20 parts of ethaboxam, 1 part of synthetic hydrated silicon oxide, 2 parts of calcium lignin sulfonate, 30 parts of bentonite and 47 parts of kaolin clay are ground and mixed, and the resultant mixture is added with water and fully kneaded, and then subjected granulation and drying so as to obtain granules.

Formulation Example 13

Forty (40) parts of metconazole, 1 part of ethaboxam, 3 parts of calcium lignin sulfonate, 2 parts of sodium lauryl sulfate and 54 parts of synthetic hydrated silicon oxide are fully ground and mixed so as to obtain wettable powders.

Comparative Formulation Example 1

Five (5) parts of tebuconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 2

Five (5) parts of triticonazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 3

Five (5) parts of ipconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 4

Five (5) parts of difenoconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 5

Five (5) parts of diniconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 6

Five (5) parts of cyproconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 7

Five (5) parts of prothioconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Comparative Formulation Example 8

Five (5) parts of bromuconazole, 20 parts of ethaboxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Seed Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable formulation prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable formulation prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

Five (5) parts of a flowable formulation prepared as in Formulation example 4, 5 parts of pigment BPD6135 (manufactured by Sun Chemical) and 35 parts of water are mixed to prepare a mixture. The mixture is used for smear treatment in an amount of 60 ml per 10 kg of dried rice seeds using a rotary seed treatment machine (seed dresser, produced by Hans-Ulrich Hege GmbH) so as to obtain treated seeds.

Seed Treatment Example 5

A powder agent prepared as in Formulation example 6 is used for powder coating treatment in an amount of 50 g per 10 kg of dried corn seeds so as to obtain treated seeds.

Seed Treatment Example 6

An emulsion prepared as in Formulation example 1 is used for smear treatment in an amount of 500 ml per 100 kg of dried sugar beet seeds using a rotary seed treatment machine (seed dresser, produced by Hans-Ulrich Hege GmbH) so as to obtain treated seeds.

Seed Treatment Example 7

A flowable formulation prepared as in Formulation example 2 is used for smear treatment in an amount of 50 ml per 10 kg of dried soy bean seeds using a rotary seed treatment machine (seed dresser, produced by Hans-Ulrich Hege GmbH) so as to obtain treated seeds.

Seed Treatment Example 8

A flowable formulation prepared as in Formulation example 3 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of sunflower seeds using a rotary seed treatment machine (seed dresser, produced by Hans-Ulrich Hege GmbH) so as to obtain treated seeds.

Seed Treatment Example 11

A powder prepared as in Formulation example 6 is used for powder coating treatment in an amount of 40 g per 10 kg of dried cotton seeds so as to obtain treated seeds.

Test Example 1

An acetone solution of ethaboxam and an acetone solution of metconazole were mixed to prepare mixed liquids containing ethaboxam and metconazole in predetermined concentration. These mixed liquids were adhered on the surface of cucumber (*Sagamihanjiro*) seeds and allowed to stand still overnight. A plastic pot was filled with sandy soil and the seeds were disseminated on it. Then the seeds were covered with sandy soil which had been mixed with a bran medium on which *Pythium ultimum*, pathogen of cucumber damping-off, had been allowed to grow. They were irrigated and allowed to grow at 18° C. under humidity for 13 days, and thereafter control effect was checked.

As a comparison, acetone solutions containing ethaboxam in the predetermined concentration and acetone solutions containing metconazole in the predetermined concentration were prepared and subjected to similar tests.

In order to calculate the control value, the incidence of disease was also determined in the case in which the seeds had not been treated with the agent.

The incidence of disease was calculated by Equation 1 and the control value was calculated by Equation 2 based on the incidence of disease.

The results are shown in Table 1.

Incidence of disease=(Number of no emerging seedlings and number of seedlings in which development of disease was observed)×100/(Number of total disseminated seeds)   "Equation 1"

Control value=100×(A−B)/A   "Equation 2";

A: Incidence of disease of plant in untreated area
B: Incidence of disease of plant in treated area Generally, the control value expected for the case in which the given two kinds of active ingredient compounds are mixed and used for the treatment, the so-called control value expectation is calculated from the following Colby's calculating equation.

$$E = X + Y - (X \times Y)/100$$ "Equation 3";

X: Control value (%) when active ingredient compound A is used for treatment in M g per 100 kg or M ppm of seeds
Y: Control value (%) when active ingredient compound B is used for treatment in N g per 100 kg or N ppm of seeds
E: Control value (%) expected for the case in which active ingredient compound A in M g per 100 kg or M ppm of seeds and active ingredient compound B in N g per 100 kg or N ppm of seeds are mixed and used for treatment (hereinbelow referred to as "control value expectation")

"Synergetic effect (%)" (Actual control value)×100/(Control value expectation)

TABLE 1

| Test compounds | | Actual control value | Control value expectation | Synergistic effect (%) |
|---|---|---|---|---|
| Ethaboxam g/100 kg-seed | Metconazole g/100 kg-seed | | | |
| 10 | 20 | 83 | 58 | 143 |
| 10 | 10 | 67 | 58 | 115 |
| 10 | 0 | 58 | — | — |
| 5 | 20 | 33 | 25 | 133 |
| 5 | 10 | 33 | 25 | 133 |
| 5 | 5 | 33 | 25 | 133 |
| 5 | 0 | 25 | — | — |
| 0 | 20 | 0 | — | — |
| 0 | 10 | 0 | — | — |
| 0 | 5 | 0 | — | — |

Test Example 2

A plastic pot was filled with sandy soil and cucumber (Sagamihanjiro) seeds were disseminated on it. Then the seeds were allowed to grow in a glasshouse for 12 days. A wettable powder of ethaboxam and a wettable powder of metconazole were individually diluted with water and then mixed to prepare mixed liquids containing ethaboxam and metconazole in predetermined concentration. These mixed liquids were sprayed to the stalk and leaves of cucumber seedlings to adhere them sufficiently on the surface of leaves of the seedlings. After spraying, the cucumber seedlings were air-dried and a PDA medium containing spores of pathogen of cucumber gray mold was placed onto the leaves of the seedlings. Then the plants were allowed to stand at 12° C. under high humidity for 6 days, and thereafter control effect was checked.

As a comparison, mixed liquids containing ethaboxam and triadimefon, mixed liquids containing ethaboxam and triadimenol, and mixed liquids containing ethaboxam and imazalil were prepared, sprayed to the stalk and leaves of cucumber seedlings to adhere them sufficiently on the surface of leaves of the seedlings, and subjected to similar tests, respectively. In addition, the above wettable powder of ethaboxam and the above wettable powder of metconazole were individually diluted with water to prepare liquids containing ethaboxam in predetermined concentration and liquids containing metconazole in predetermined concentration and then subjected to similar tests.

The incidence of disease was calculated by Equation 4 and the control value was calculated by Equation 2 based on the incidence of disease.

The results are shown in Table 2.

Incidence of disease=(diameter of leaf spot of plant in treated area)/(diameter of leaf spot of plant in untreated area)×100   "Equation 4"

TABLE 2

| Test compounds | Actual control value | Control value expectation |
|---|---|---|
| Ethaboxam (12.5 ppm) + Metconazole (12.5 ppm) | 22.5 | 0 |
| Ethaboxam (12.5 ppm) | 0 | 0 |
| Metconazole (12.5 ppm) | 0 | 0 |
| Ethaboxam (12.5 ppm) + Triadimefon (12.5 ppm) | 0 | 0 |
| Ethaboxam (12.5 ppm) + Triadimenol (12.5 ppm) | 0 | 0 |
| Ethaboxam (12.5 ppm) + Imazalil (12.5 ppm) | 0 | 0 |

INDUSTRIAL APPLICABILITY

According to the present invention, a composition for controlling plant diseases having high activity, and a method for effectively controlling plant diseases can be provided.

The invention claimed is:

1. A composition for controlling plant diseases comprising, as active ingredients, ethaboxam and metconazole.

2. The composition according to claim 1, which has a weight ratio of ethaboxam to metconazole falling within the range of from 1:0.01 to 1:50.

3. A seed treatment agent comprising, as active ingredients, ethaboxam and metconazole.

4. A plant seed treated with effective amounts of ethaboxam and metconazole.

5. A method for controlling plant diseases which comprises applying, to a plant or a locus where a plant is allowed to grow, effective amounts of ethaboxam and metconazole.

6. A method for controlling plant diseases according to claim 5, wherein the plant diseases are plant diseases caused by *Oomycetes*.

* * * * *